United States Patent [19]
Hnilica et al.

[11] Patent Number: 5,798,832
[45] Date of Patent: Aug. 25, 1998

[54] PROCESS AND DEVICE FOR DETERMINING ELEMENT COMPOSITIONS AND CONCENTRATIONS

[75] Inventors: Klaus D. Hnilica, Rodenbach; Klaus Schneider, Mannheim, both of Germany

[73] Assignee: NIS Ingenieurgesselschaft MBH, Hanau, Germany

[21] Appl. No.: 737,443
[22] PCT Filed: Apr. 28, 1995
[86] PCT No.: PCT/EP95/01625
  § 371 Date: Feb. 24, 1997
  § 102(e) Date: Feb. 24, 1997
[87] PCT Pub. No.: WO95/30140
  PCT Pub. Date: Nov. 9, 1995

[30] Foreign Application Priority Data

May 2, 1994 [DE] Germany ............ 44 15 381.3

[51] Int. Cl.$^6$ ........................................ G01N 21/63
[52] U.S. Cl. ........................................ 356/316; 356/318
[58] Field of Search ........................... 356/316, 318

[56] References Cited

U.S. PATENT DOCUMENTS

| | | | |
|---|---|---|---|
| 4,645,342 | 2/1987 | Tanimoto et al. | 356/318 |
| 4,833,322 | 5/1989 | Forster et al. | 356/316 |
| 4,986,658 | 1/1991 | Kim | 356/318 |
| 4,995,723 | 2/1991 | Carlhoff et al. | 356/318 |
| 5,283,417 | 2/1994 | Misawa et al. | 356/318 |
| 5,379,103 | 1/1995 | Zigler | 356/318 |
| 5,446,538 | 8/1995 | Noll | 356/318 |

FOREIGN PATENT DOCUMENTS

| | | |
|---|---|---|
| 0293983 | 5/1988 | Germany. |
| 4004627 | 2/1991 | Germany. |
| 0476728 | 8/1991 | Germany. |
| 0549902 | 11/1992 | Germany. |
| 4138157 | 5/1993 | Germany. |
| WO9221957 | 12/1993 | WIPO. |

OTHER PUBLICATIONS

Time–Resolved Laser Induced Breakdown Spectroscopy of Iron Ore—K.J. Gant et al. Dec. 10, 1990, vol. 44 No. 10.

*Primary Examiner*—David C. Nelms
*Assistant Examiner*—Zandra V. Smith
*Attorney, Agent, or Firm*—Isaf, Vaughan & Kerr

[57] ABSTRACT

The invention pertains to a process and a device for determining the composition and concentration of elements in material samples using laser-based plasma emission spectroscopy. The process comprises the following steps: a) transformation of a portion of the material sample (20) to be analysed to a plasma-like state (46) by means of a pulsed high-power laser (12) focussed on the material sample (20); b) spectral analysis of the radiation emitted by the plasma (46) using a spectrometer (26); c) measurement of the total emission spectrum (44) of the plasma (46) changing per laser pulse in one or more spectral ranges typical of the element, using a detector (40); and d) calculation of the composition and concentration of the elements based on the entire spectrum (44) of measured emissions, i.e. the sum of a number of measured individual spectra (42). The claimed device (10) comprises a high-power laser (12), a spectrometer (26) and at least one measuring head (14) with integrated radiation optics (22). The high-power laser (12) and the spectrometer (26) are geometrically and stereoscopically decoupled from the measuring head and are connected to each other via at least one waveguide.

10 Claims, 6 Drawing Sheets

MEASURED SPECTRA FOR SAMPLE OF INORGANIC MATERIAL

FIG. 1a

MEASURED SPECTRA FOR SAMPLE OF INORGANIC MATERIAL

FIG. 1b

MEASURED SPECTRA FOR SAMPLE OF INORGANIC MATERIAL

FIG. 1c

MEASURED SPECTRA FOR SAMPLE OF INORGANIC MATERIAL

PROCESS AND DEVICE FOR DETERMINING ELEMENT COMPOSITIONS AND CONCENTRATIONS

FIELD OF THE INVENTION

The present invention relates to a process for determining the composition and concentration of elements in material samples, in particular for determining the concentration or the presence of precious metals in unsorted metal scrap by means of laser-based plasma emission spectroscopy, as well as a device therefor comprising a high-power laser, a spectrometer and a measuring head including integrated radiation optics.

BACKGROUND OF THE INVENTION

The detection of element concentrations near the surface through spectral analysis of laser-induced plasma is discussed in the relevant literature under the key words of LIBS (=laser-induced breakdown spectroscopy) and laser spark spectroscopy. Such processes are used in particular for analysing metal particles. The specification of German laid-open patent application DE-OS 37 18 672 A1 for example discloses a process for determining or analysing the composition of metal particles which one after the other pass through a test line, in which said particles are subjected to a pulsed laser beam, partly evaporated to plasma and the plasma spectral lines are analysed to identify the metal particles. In this known process, a certain small wavelength range or a certain wavelength is filtered out of the total radiation emitted by the plasma and only the intensity of the partial radiation filtered out, i.e. only a certain wavelength or wavelength range is compared with an example to obtain a qualitative analysis of the elements contained in the sample.

A process described in the specification of German laid-open patent application DE-OS 40 28 102 A1 likewise relates to the analysis of metal particles of different material compositions. By means of a pulsed laser, a plasma is generated, thus ablating metal from the metal to be analysed. Discrete spectral lines or spectral line ranges are also filtered out of the plasma line spectrum. In doing so, a characteristic value is formed according to an algorithm based on the radiation intensities of the wavelengths of the spectral lines or spectral line ranges filtered out, and a sorting signal is obtained by comparing said characteristic value with given limits. Also in this process the metal particles are subjected to a qualitative analysis.

The disadvantages of these known processes are that they are merely intended for conducting qualitative analyses, with low accuracy of the resulting analyses. A high accuracy of the analysis is not required for said known processes since they are only aimed at producing a sorting signal for coarsely categorizing particles of different metals into certain element groups. However, it has turned out that a merely qualitative analysis of materials such as metal particles or metal scraps is no longer sufficient to ensure an economically reasonable separation and reclaiming of e.g. metallic raw materials.

The specification of German patent DE 41 18 518 C2 describes a process for conducting the laser-based emission spectroscopy in which plasma parameters such as plasma temperature and plasma density are measured. In order to obtain a quantitative analysis, the emission spectra are only to be measured in defined plasma states which are produced by influencing the intensity of the laser radiation which forms the plasma. One shortcoming of this process is that a lot of constructive work and calculations are required for carrying out the process, resulting in a noticeably increased fault liability of the process and the required device.

It is the object of the present invention to provide a process of the above specified type by means of which a simple quantitative and qualitative analysis of high accuracy can be conducted.

It is a further object of the invention to provide an device of the above specified type.

Known devices for determining the composition and concentration of elements by means of laser-based plasma emission spectroscopy comprise a source of laser light generating pulsed laser beams, one or several spectral filters with respective spectral detectors as well as means for electronically evaluating the spectral images obtained. One disadvantage of these known devices is that the laser source and the spectrometers themselves contain the necessary optical means such as lens systems. Consequently, the resulting large dimensions of the devices alone limit their possibilities of use.

Since the devices mentioned have to operate at relatively short focal lengths so as not to excessively increase the energy consumption of the laser, it is moreover necessary to bring the devices as close as possible up to the material samples to be analysed. When the known devices are used, care must also be taken that the sensitive integrated laser or spectrometer control means are not exposed to extreme physical conditions such as temperature or pressure. This further limits the possible applications of the known devices for determining element compositions and concentrations of material samples by means of laser-based plasma emission spectroscopy.

Furthermore a device for conducting a process for determining material properties of polymerous materials is known from German patent application DE 40 04 627. This device comprises deviation mirrors and beam splitters for guiding a laser beam and/or for returning the plasma radiation to a spectrograph. Due to this structure the possible positioning range of this device is very restricted since the maximum possible distance between the actual measuring optics and the laser source and/or the spectrograph is very limited.

Moreover, German patent application DE 41 38 156 A1 discloses a device for conducting a process for determining the thickness of a coating using laser radiation. Also with this device no free flexible positioning of the measuring system with respect to a material sample to be examined is possible, due to the specific structure of said device.

It is therefore a further object of the present invention to provide a device of the aforementioned type which ensures an as wide as possible application range.

The invention further provides a measuring head for the above mentioned device. In order to be independent of the different surface structures of the material samples to be analysed, it is necessary to operate with relatively large focal lengths when focussing the laser beam which are actually undesired—as already set out above. In addition to the increased energy consumption resulting therefrom, the plasma generation conditions also distinctly vary when the known devices are used. In order to avoid such variations, it has been suggested in the specification of German laid-open patent application DE-OS 40 28 102 A1 that only metal particles below a certain particle size be analysed, said particles—arranged one after the other to form a line—individually pass the measuring means. An exact positioning of the focal point of the known device on the sample surface is still not possible, causing the above-mentioned variations of the plasma generation conditions.

It is therefore another object of the present invention to provide a measuring head for a device of the above-mentioned type, by means of which the focal point of the laser beam can be accurately positioned on the sample surface.

In accordance with a first step a) of the process of the invention, a portion of a material sample to be analysed is transformed to a plasma-like state by means of a pulsed high-power laser focussed on the material sample. In a further step b) of the process according to the invention, the radiation emitted by the plasma is spectrally analysed by means of a spectrometer. In a third step c) of the process, the total emission spectrum of the plasma changing per laser pulse is measured in one or more selected spectral ranges typical of the element, using a detector. In a fourth and final process step d) the composition and concentration of the elements are then calculated in the manner set out above.

In an advantageous embodiment of the process according to the invention the high-power laser is a frequency-multiplying Nd:YAG type laser emitting radiation of a wavelength of 532 nm or 353 nm. When wavelengths in the visible or ultraviolet range are used, it is possible to obtain more constant emission spectra, thus further improving the accuracy of the analysis and optimizing the analysis range. In addition, it has been found that when a Nd:YAG type laser of these wavelengths is used, no melting processes occur on the surface of the material sample which might lead to pronounced variations in the plasma itself during the plasma formation. The material sample to be analysed is rather evaporated spontaneously so that only minimal variations occur during the plasma formation, likewise resulting in more constant emission spectra over the entire duration of the measuring process which in turn increases the accuracy of the analysis obtained by this process.

In a further advantageous embodiment of the process according to the invention, the laser is focussed in procedural step a) in that a measuring head is put on the material sample. The measuring head comprises a casing having radiation optics in its interior which is mounted at a defined constant distance from the exit opening of the casing such that the focal point of the laser beam is in the plane of the exit opening. In this manner, different surface contours or different dimensions of the sample material to be analysed can be compensated. In view of the predefined and constant distance between the exit opening of the casing and the radiation optics, the laser beam is always optimally focussed. Moreover, an advantageously small focussing distance is possible in this manner, such that the laser can be operated with low energy. Advantageously the laser pulse energy on the material sample is 1 to 10 mJ. Furthermore, the advantage is obtained that due to the exact focussing of the laser depth profiles of the element composition or concentration of the material sample can be obtained.

In a further advantageous embodiment of the invention the measuring head comprises at least one movable spacer, said spacer—in a first position thereof—partially projecting from the side of the casing facing the sample to be analysed and—in a second position thereof—being inside the casing. In its second position, the spacer releases a laser source trigger means. This ensures that the laser is only triggered after the measuring head has been put onto the material sample, thereby focussing the laser. This in turn ensures that the plasma formation conditions merely vary to a minimal extent during the measuring process or processes.

In yet a further advantageous embodiment of the invention, the detector used in process step c) is a multi-channel detector. The multi-channel detector may include photodiode arrays or CCD arrays or lines provided with photomultipliers. In this manner, a simultaneous analysis of the entire plasma emission spectrum analyzed spectrally is advantageously possible.

In a further advantageous embodiment of the process according to the invention, the plasma emission are time-filtered in process step c) using an optical transmission switch. This filtering comprises extracting the wide-band emission background in a period of 0 to 500 nsec after a laser pulse and/or extracting molecular and/or cluster spectra in a period in the μsec to msec time range after a laser pulse. As an advantage resulting therefrom, the accuracy of the analysis can be increased on the one hand and the amount of data to be processed is reduced on the other.

The entire emission spectrum analysed according to process step d) may be evaluated using different advantageous calculation methods. The element compositions and concentrations may for example on the one hand be calculated by means of mathematical correlation functions using one or several calibration spectra of one or several calibration samples of known element composition and concentration. Advantageously, a cross correlation function is used for this purpose. On the other hand, such calculation can also be carried out by means of an integration of several individual measurements or spectra, with the pulse to pulse variations of the individual spectra being averaged during plasma formation. Such integration can be advantageously conducted in the detector. In this manner, a reduction of the data flux to be processed is also ensured, such that lasers of a very high repeat rate or pulse rate can be used. However, the individual measurements can also be integrated by means of a data processing system following after the detector which uses appropriate software. However, the accuracy of the analysis can also be increased according to the invention, when the entirety or a subset of element-typical spectral lines are used for calculating the concentrations of individual elements.

In a device according to the invention for determining the composition and concentration of elements in material samples, the high-power laser and the spectrometer are geometrically and stereoscopically decoupled from the measuring head in accordance with the invention, said measuring head being coupled with the laser and/or the spectrometer via at least one optical waveguide. In view of the fact that the laser, the spectrometer and the measuring head are decoupled, it is possible to arrange the sensitive laser and spectrometer means at spatial positions different from that of the measuring head which is positioned on the material sample to be analysed. This ensures that the measuring head, if constructed appropriately, e.g. by selecting a suitable material, can be used in extreme temperature and pressure conditions without any damage being done to the laser source or the laser control means or the spectrometer.

In addition, the optical waveguide advantageously ensures a low loss transport of the plasma emission to a spectrometer. Furthermore, the use of optical waveguides enables the laser beam to measure simultaneously at several different measuring positions after it has been split up into several optical waveguides. This advantageously increases the speed of the analysis.

At least one optical waveguide is used for transmitting the plasma emissions to the spectrometer. Due to the fact that the plasma emissions are focussed on the second optical waveguide having the same radiation optics as is used for focussing the laser, the overall structure of the measuring head is simple and robust. Since several optical waveguides are provided for transmitting the plasma emission spectra to the radiation optics, a further advantage is obtained in that the measuring time for an individual measurement is minimized thereby.

In yet another advantageous embodiment, the high-power laser comprises a frequency-multiplying Nd:YAG type laser. The advantages of this laser type have already been set out above. The same is true for the use of a multi-channel detector in the device according to the invention.

Furthermore, a measuring head for the device according to the invention is proposed, comprising radiation optics arranged in a casing, said casing including at least one movable spacer. The spacer—in a first position thereof— partially projects from the side of the casing which faces the sample to the analysed and—in a second position thereof— is completely inside the casing. In this second position the spacer releases a laser trigger means. This ensures that the laser pulse only occurs after the actual casing of the measuring head has been installed and the laser beam has consequently been accurately positioned and focussed. In this manner, unevennesses in the surface of the material sample to be measured can be compensated.

In yet a further advantageous embodiment, the radiation optics is mounted at a defined constant distance from an exit opening of the casing, so that the focal point of the laser beam is in the plane of the exit opening. Such arrangement advantageously results in that the laser may always be focussed and operated at a constant focal distance, which reduces the amount of laser pulse energy on the material sample. Typically, the amount of laser pulse energy on the material sample is 1–10 mJ. The radiation optics is advantageously mounted at a distance of 25 to 40 mm from the exit opening of the casing.

BRIEF DESCRIPTION OF THE DRAWINGS

Further details, features and advantages of the invention may be gathered from the following description of embodiment examples illustrated in the attached drawings in which.

DETAILED DESCRIPTION OF THE INVENTION

Figure 3:
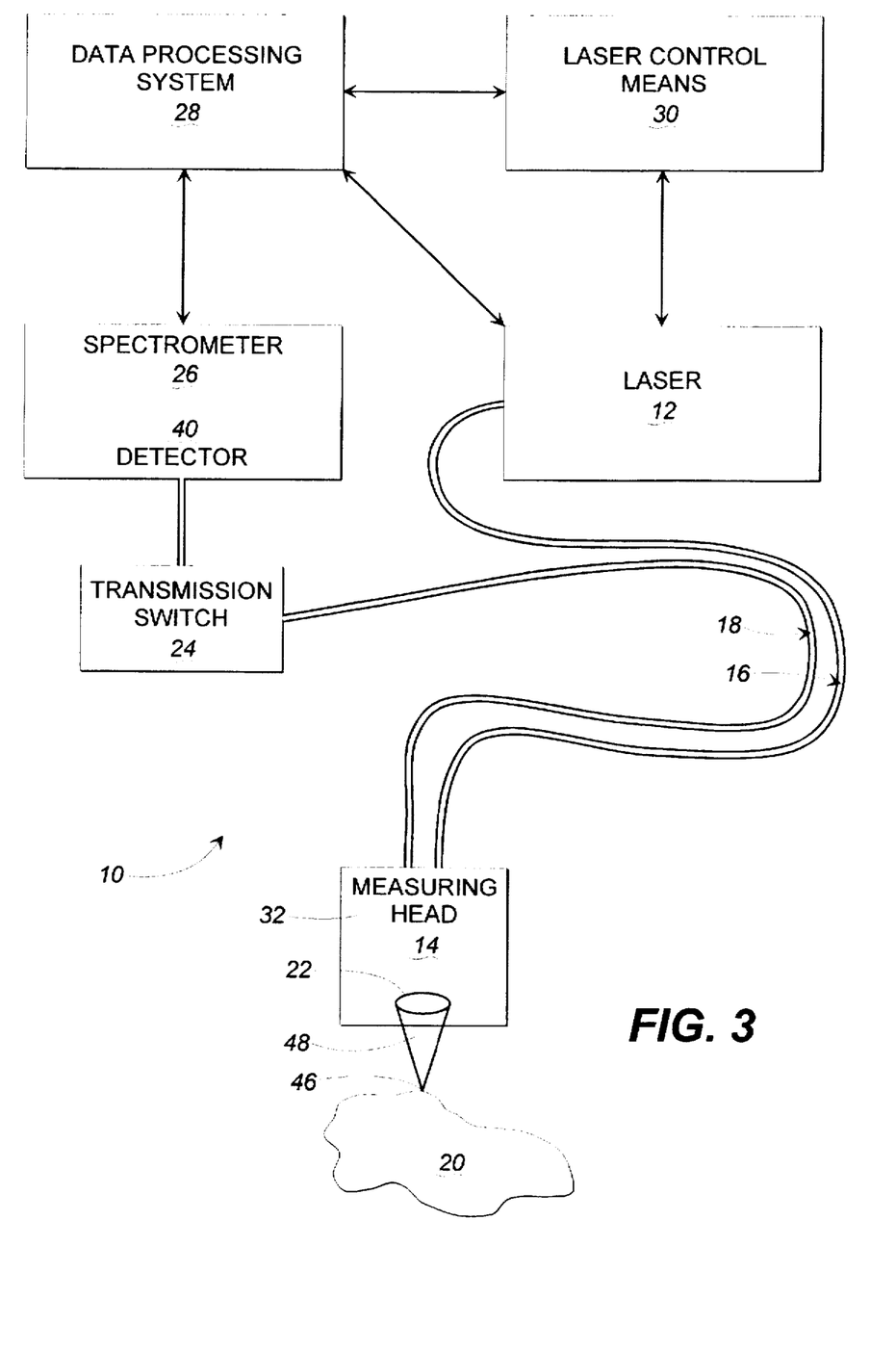
FIG. 3 is a perspective view of the device according to the invention.
Figure 4:
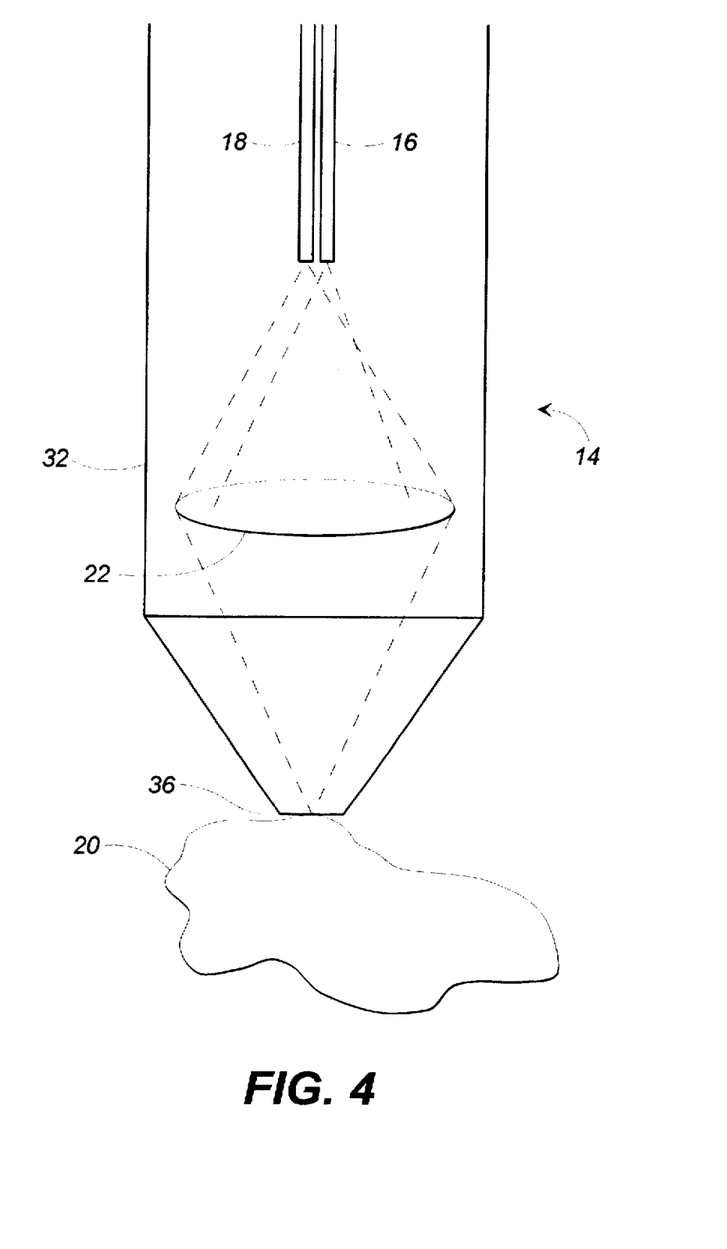
FIG. 4 is a perspective view of the measuring head of the device according to the invention.

With reference to FIG. 3, a material sample 20, i.e. a steel sample, is exposed to laser radiation 48 emitted by a laser 12. According to a first process step a) a portion of the material sample 20 is transformed to a plasma-like state 46. The high-power laser 12 is pulsed and comprises a frequency-multiplying Nd:YAG type laser. The excitation radiation of the Nd:YAG type laser has a wavelength of 1064 nm or shorter wavelengths (in the case of frequency multiplication) of 532 nm or 355 nm. The pulse energy of the laser 12 on the material sample 20 is 1 to 10 mJ. The pulse rate of the laser 12 is 10 to 500 Hz, preferably 30 to 100 Hz. The pulse duration typically is 10 nsec. The laser 12 is focussed with regard to the material sample 20 in that a measuring head 14 (see FIG. 4) is positioned on the material sample 20. As can be seen in FIG. 4, the measuring head 14 comprises a casing 32, in the interior of which there is radiation optics 22 mounted at a defined constant distance from an exit opening 38 of the casing 32, in such a manner that the focal point of the laser beam is in the plane of the exit opening 38. This results in an exact positioning of the focal point on the surface of the sample so that any variations of the conditions of plasma formation can be minimized. Moreover, the distance of the measuring head 14 from the sample 20 can be minimized which also results in considerable reduction of the required laser energy. Typically, amounts of laser energy in a range of 5 mJ are used.

Figure 5:
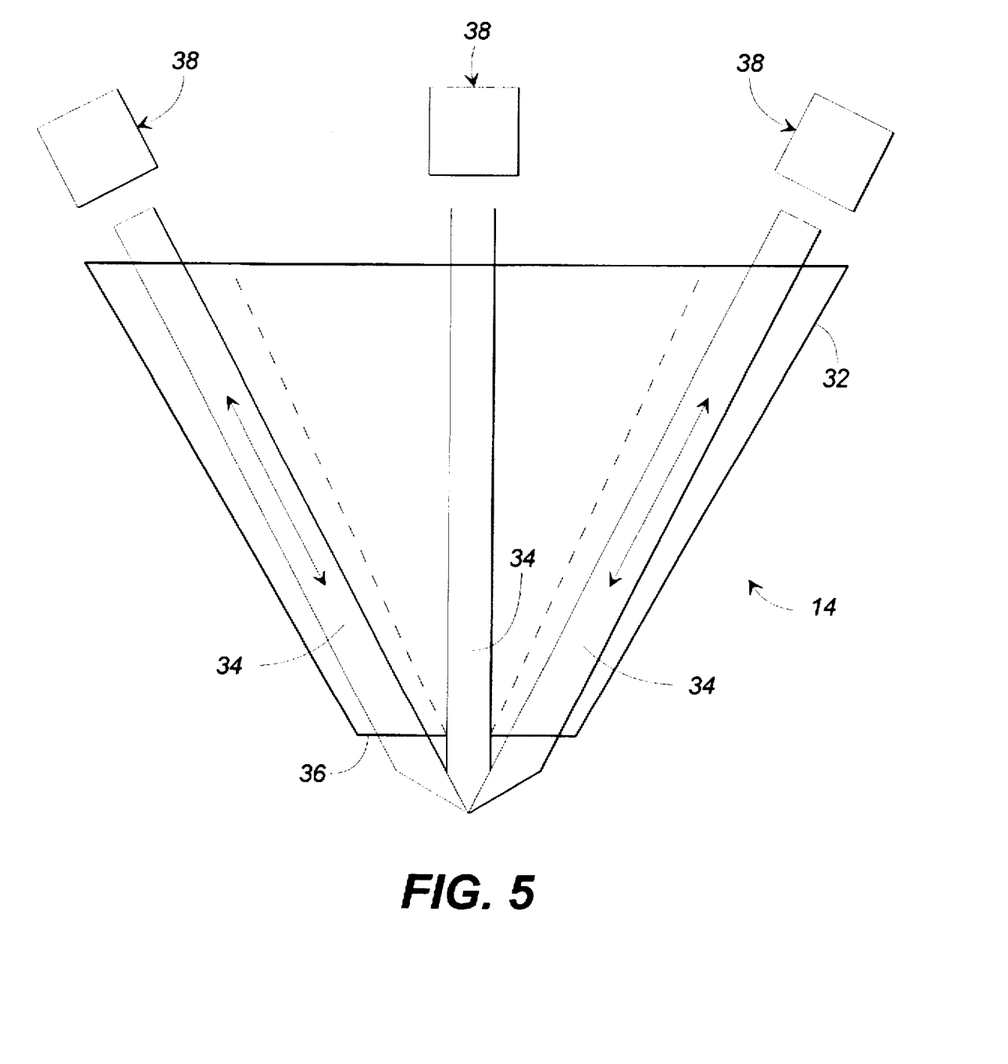
FIG. 5 is a perspective view of a further embodiment example of a measuring head of the device according to the invention.

In order to ensure that the laser 12 is accurately positioned and focussed on the material sample 20, at the same time preventing a laser pulse from being triggered before the measuring head 14 has finally been positioned on the material sample 20, the measuring head 14 may include—in an embodiment example shown in FIG. 5—at least one movable spacer 34 mounted in or on the casing 32. The spacer 34—in a first position thereof—partially projects from the side of the casing 32 which faces the sample 20 to be analysed and—in a second position thereof—is completely inside the casing 32. The spacer will only release a triggering means 38 for the laser 12 when the spacer 34 is in its second position.

In a second step b) of the process according to the invention, the radiation emitted by the plasma 46 is analyzed spectrally by means of a spectrometer 26 as shown in FIG. 3.

In a further step c) of the process according to the invention, the entire emission spectrum 44 of the plasma 46 changing per laser pulse is measured in one or more spectral ranges by means of a detector 40 as shown in FIG. 3. The detector 40 comprises a multi-channel detector. Due to the use of a multi-channel detector it is possible to simultaneously detect the entire plasma emission spectrum which has been spectrally analyzed. Photodiode arrays, CCD arrays, lines provided with photomultipliers or similar detectors may be used as detectors 40.

In step c) of the process the plasma emissions may additionally be time-filtered by means of an optical transmission switch 24. This filtering comprises extracting the wide-band emission background in a period of 0 to 500 nsec after a laser pulse and/or extracting molecular and/or cluster spectra in a period in a μsec to msec range after a laser pulse. This filtering results in a reduction of the data which in turn facilitates and accelerates the digitalisation and storage of the spectrum measured.

In a further step d) of the process of the invention, the element composition and concentration of the analysed material sample 20 is calculated based on the total emission spectrum 44. The total emission spectrum 44 measured is the sum of a number of individual spectra 42 measured. In order to accomplish the desired quantitative accuracy of the analysis, at least five, preferably 10 to 100 individual spectra 42 are evaluated, i.e. combined to an entire spectrum 44.

FIGS. 1a–1d are diagrams of four measured individual spectra 42 of the inorganic material sample 20 (steel sample). In this diagram, the intensities of the emission radiation are plotted on the ordinate, whereas the respective wavelength is plotted on the abscissa. The emission spectrum includes a wavelength range of approx. 45 nm. From a comparison of the emission spectra of the same material sample, which have been taken at different times, it can be seen that—although the individual spectra are considerably different in their intensities at individual wavelengths— taken together, they nevertheless reflect relatively constant conditions of plasma formation.

Figure 1A:
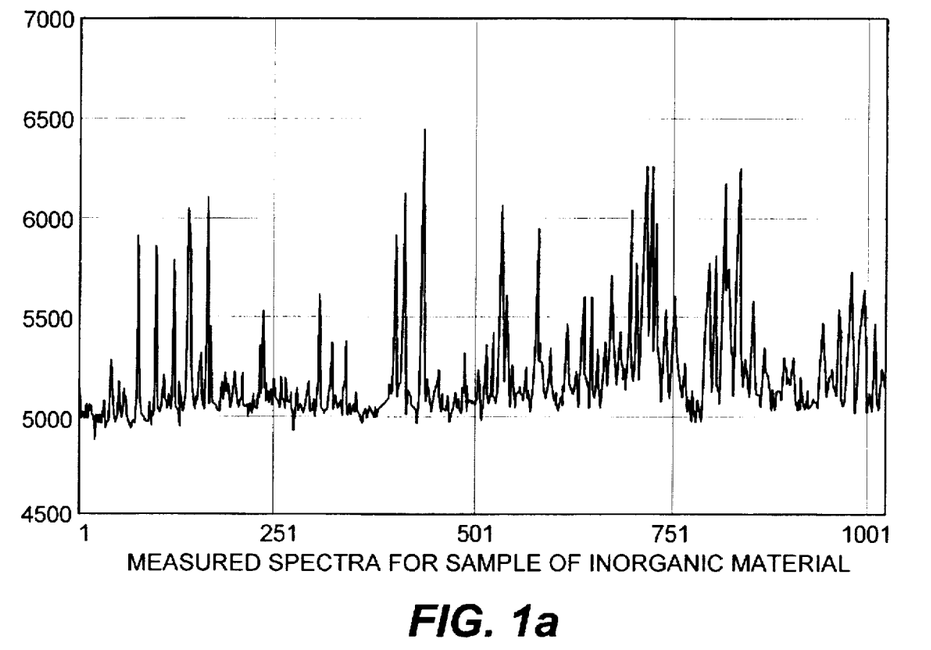
FIGS. 1a–1d are diagrams of four measured individual spectra of a sample of inorganic material.
Figure 1B:
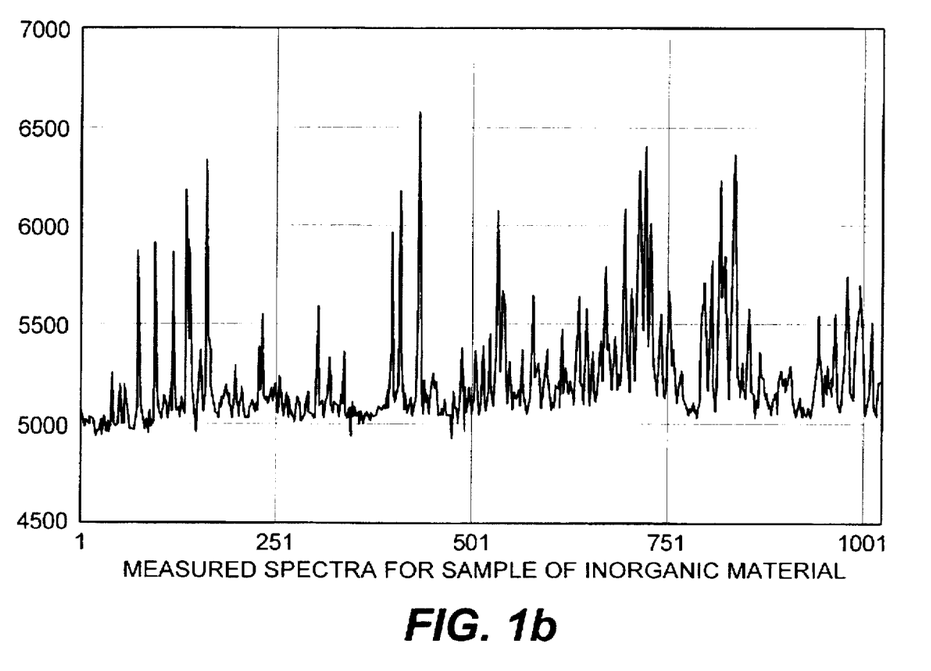
Figure 1C:
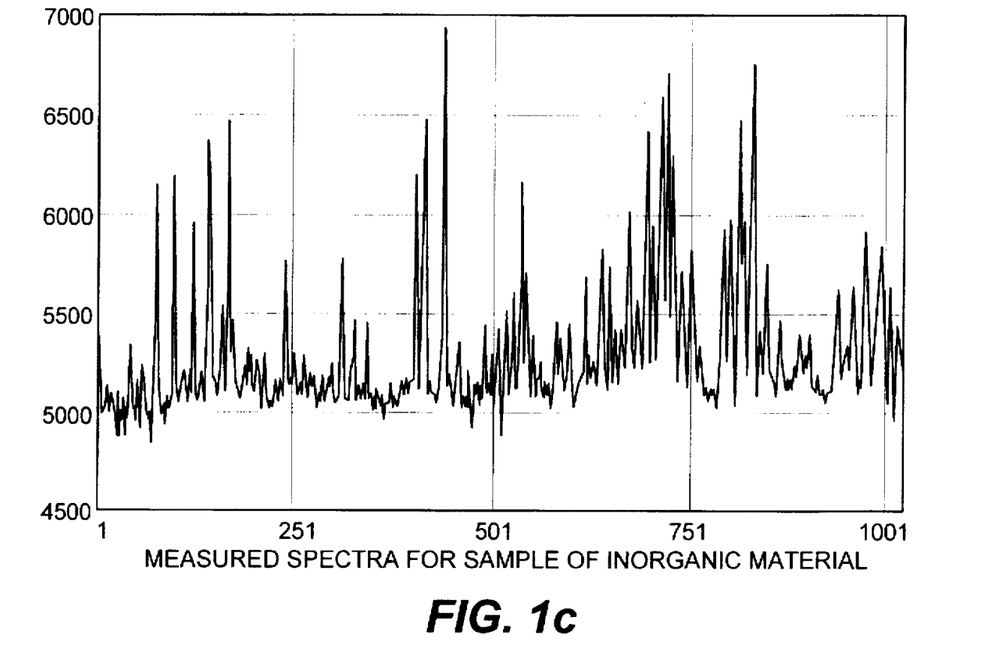
Figure 1D:
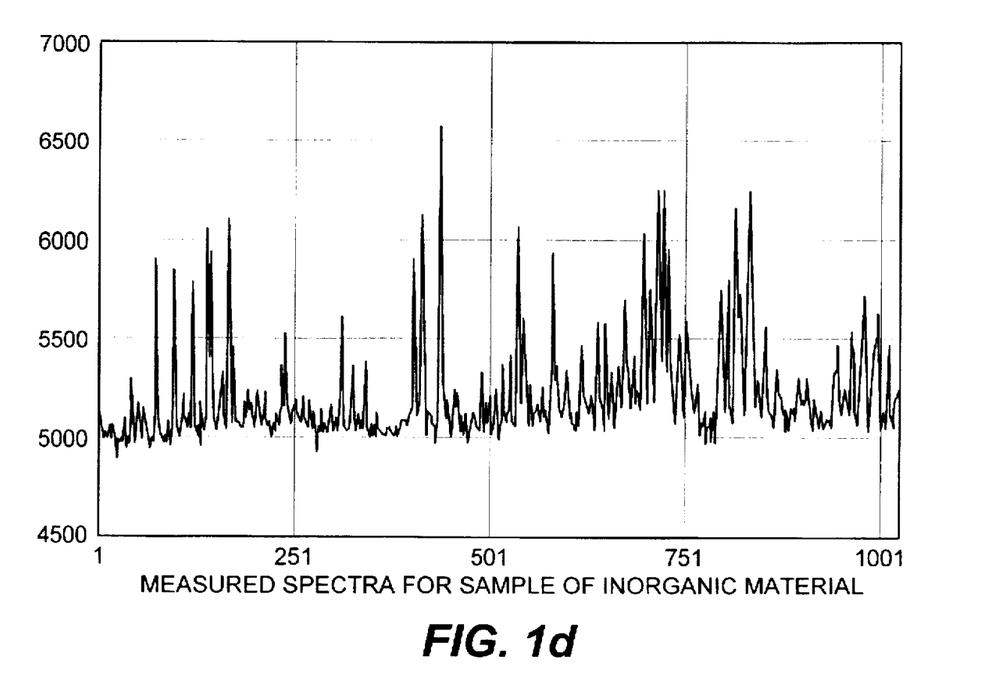
Figure 2:
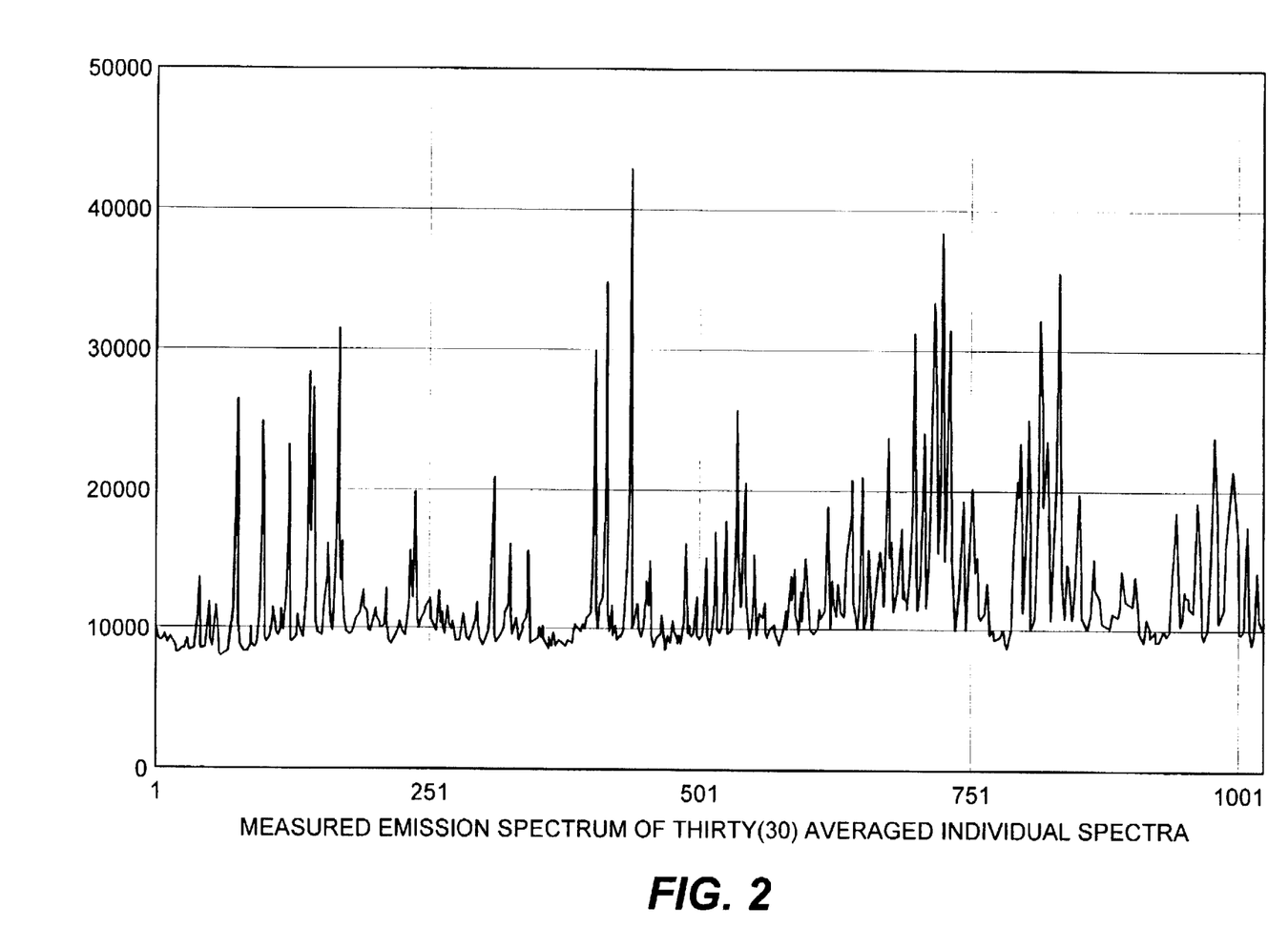
FIG. 2 is a diagram of an entire measured emission spectrum of 30 averaged individual spectra.

FIG. 2 is a diagram of an entire emission spectrum 44 measured of the same material sample 20 which is taken as a basis for the calculation of the element composition and concentration in accordance with step d) of the process according to the invention. The entire emission spectrum 44 shown is obtained by an integration of 30 individual measurements or spectra 42, with the pulse to pulse variations of the individual emission spectra 42 being averaged during the plasma formation. This considerably increases the accuracy of the analysis. The individual measurements 42 can be integrated in the detector 40. This means that the detector data is integrated before it is read out, and consequently only a reduced data flux is obtained for evaluation in a subsequent data processing system 28. In view of the reduced data flux lasers having a very high repeat rate can be used. In particular, this is true for lasers having pulse rates of >30 Hz. However, it is also possible to integrate the individual measurements directly in the data processing system 28 following after the detector.

In order to obtain the desired high accuracy of the analysis, however, it is also possible to calculate the element compositions and concentrations according to process step d) by means of mathematical correlation functions using one or several calibration spectra of one or several calibration samples of known element composition and concentration. Preferably, a cross correlation function is used for this purpose. However, it is also possible to use other specific correlation functions for evaluating the entire spectrum 44 measured.

FIG. 3 is a perspective view of a device 10 for determining the composition and concentration of elements in material samples. The device 10 comprises a laser 12, a spectrometer 26 and a measuring head 14 including integrated radiation optics 22. One can see that the high-power laser 12 and the spectrometer 26 are geometrically and stereoscopically decoupled from the measuring head 14. The measuring head 14 is coupled with the laser 12 via an optical waveguide 16. The measuring head 14 is further coupled with the spectrometer 26 via a second optical waveguide 18. The laser beam from the laser or the laser source 12 is coupled into the optical waveguide 16. Due to the use of the optical waveguide 16, the laser beam may be transported to the measuring head 14 with only low loss. A typical attenuation of the laser beam is in the range of approx. 1 unit per km of transport distance. The high-power laser 12 preferably comprises a frequency multiplying Nd:YAG laser. However, other suitable types of laser may also be employed. The illustrated device 10 further comprises a transmission switch 24 provided between the radiation optics 22 and the spectrometer 26 in the path of the optical waveguide 18. The transmission switch 24 comprises a Pockels cell. A detector 40, i.e. a multi-channel detector, is provided in the spectrometer 26. This detector 40 can consist of photodiode arrays, CCD arrays or lines provided with photomultipliers. Other kinds of detectors of similar properties may also be used.

The data processing system 28 is used, on the one hand, for evaluating the measured entire spectra 44 or for the calculation of the element compositions and concentrations, and, on the other hand, the laser 12 is controlled by means of said system 28. Such control may be of a direct nature, or it may also be effected via a laser control means 30 connected with the data processing system 28 and arranged separately. Moreover, this data processing system 28 may be employed for controlling automated positioning systems for positioning the measuring head 14.

In an embodiment example which is not illustrated several measuring heads 14 can be connected with the laser 12 via several optical waveguides 16. The splitting up of the laser beam accomplished in this manner makes simultaneous measurements at several different measuring sites possible. This is only made possible by the process and the device according to the present invention since in accordance therewith only minimal amounts of laser energy are required for each laser position. However, it is also conceivable to employ several optical waveguides 18 for transmitting the plasma emission spectra from one or several measuring heads 14 to the spectrometer 26. When several multi-channel detectors or one multi-channel detector with a planar, two-dimensional array of individual detectors 40 are used simultaneously, this will result in a significant minimization of the measuring time required for each individual measurement.

Owing to the geometrical separation of sensitive elements of the device 10, such as the laser source 12 or the spectrometer 26, via one or several optical waveguides 16, 18, the illustrated device 10 is suited for use in rough ambient conditions, e.g. in steelmills, in scrap yards, in the open air, in nuclear areas.

FIG. 4 is a perspective view of the measuring head 14 of the device 10. It is seen that the laser beam is first expanded and subsequently highly focussed by means of the radiation optics 22 inside the measuring head 14. The said radiation optics 22 can comprise a single lens or a lens system. The laser beam is focussed in such a manner that the focal point of the laser beam is in the plane of an exit opening 36. Typical focal lengths are between 25 and 40 mm. Since the radiation optics 22 is mounted at a defined constant distance from the exit opening 36 of the casing 32, the laser will always be focussed with the same constant focal distance after the measuring head 14 has been put onto the material sample 20.

FIG. 5 is a perspective view of a further embodiment example of the measuring head 14 of the device 10. The measuring head 14 comprises at least one movable spacer 34 mounted in or on the casing 32. The spacer 34—in a first position thereof (as illustrated in the Figure)—partially projects from the side of the casing 32 which faces the sample 20 to be measured. In this first position, the three spacers illustrated in the embodiment example contact each other—which results in a kind of closure of the exit opening 36. In a second position, the spacers 34 are completely inside the casing 32. In this position, the spacers release a triggering means 38 for the laser 12. This triggering means 38 may be released mechanically, electronically or in any other suitable manner.

We claim:

1. A process for determining element compositions and concentrations of material samples, in particular for determining the concentration or the presence of precious metals in unsorted metal scrap, by means of laser-based plasma emission spectroscopy, said process comprising the following steps:

a) transforming a portion of the material sample (20) to be analyzed to a plasma-like state (46) by means of a pulsed high-energy laser (12) focused on the material sample (20), the plasma emitting radiation characteristic of the material sample;

b) performing spectral analysis of the radiation emitted by the plasma (46) using a spectrometer (26);

c) measuring the total emission spectrum (44) of the plasma (46) changing per laser pulse in one or more spectral ranges typical of the element, using a detector (40);

wherein the composition and concentration of the material samples are calculated in a further procedural step d) based on the entire spectrum (44) of measured emissions, said calculation being effected by integrating several individual measurements or spectra (42), the pulse to pulse variations of the individual spectra (42) being integrated during plasma formation, the individual measurements being integrated in the detector (40);

step a) being performed by positioning a measuring head (14) on the material sample (20);

the measuring head (14) comprising a casing (32) inside of which there is provided radiation optics (22) at a defined constant distance from an exit opening (38) of the casing (32), the focal point of the laser beam being in the plane of the exit opening;

the casing (32) including at least one movable spacer (34), said spacer (34)—in a first position thereof—partially projecting from the side of casing (32) which faces the sample (20) to be measured and—in a second position thereof—being completely inside the casing (32), said spacer (34)—in its second position—releasing a trigger means (38) for the laser source (12).

2. A process for determining element compositions and concentrations of material samples, in particular for determining the concentration or the presence of precious metals in unsorted metal scrap, by means of laser-based plasma emission spectroscopy, said process comprising the following steps:

a) transforming a portion of the material sample (20) to be analyzed to a plasma-like state (46) by means of a pulsed high-energy laser (12) focused on the material sample (20), the plasma emitting radiation characteristic of the material sample;

b) performing spectral analysis of the radiation emitted by the plasma (46) using a spectrometer (26);

c) measuring the total emission spectrum (44) of the plasma (46) changing per laser pulse in one or more spectral ranges typical of the element, using a detector (40);

wherein the composition and concentration of the material samples are calculated in a further procedural step d) based on the entire spectrum (44) of measured emissions, said calculation being effected by integrating several individual measurements or spectra (42), the pulse to pulse variations of the individual spectra (42) being integrated during plasma formation, the individual measurements being integrated in the detector (40);

wherein in process step c) the plasma emissions are filtered in time by means of an optical transmission switch (24).

3. The process of claim 2 wherein said filtering comprises extracting the wide-band emission background in a time period of from 0 to 500 nsec after a laser pulse and extracting spectra within a time period from 1 μsec to 999 msec after the laser pulse.

4. The process of claim 2 wherein said transmission switch (24) is a Pockels cell.

5. A process for determining element compositions and concentrations of material samples, in particular for determining the concentration or the presence of precious metals in unsorted metal scrap, by means of laser-based plasma emission spectroscopy, said process comprising the following steps:

a) transforming a portion of the material sample (20) to be analyzed to a plasma-like state (46) by means of a pulsed high-energy laser (12) focused on the material sample (20), the plasma emitting radiation characteristic of the material sample;

b) performing spectral analysis of the radiation emitted by the plasma (46) using a spectrometer (26);

c) measuring the total emission spectrum (44) of the plasma (46) changing per laser pulse in one or more spectral ranges typical of the element, using a detector (40);

wherein the composition and concentration of the material samples are calculated in a further procedural step d) based on the entire spectrum (44) of measured emissions, said calculation being effected by integrating several individual measurements or spectra (42), the pulse to pulse variations of the individual spectra (42) being integrated during plasma formation, the individual measurements being integrated in the detector (40);

the element compositions and concentrations being calculated in process step d) by means of mathematical correlation methods using one or several calibration spectra of one or several calibration samples of known element composition and concentration;

wherein a cross correlation method is used as the mathematical correlation method in step d).

6. A device for determining element compositions and concentrations of material samples and specifically for determining the concentration or the presence of precious metals in unsorted metal scrap, by means of laser-based plasma emission spectroscopy, said device comprising a high-power laser (12), a spectrometer (26), and at least one measuring head (14), said high-power laser (12) and said spectrometer (26) being geometrically and stereoscopically decoupled from said measuring head (14) wherein said measuring head (14) includes integrated radiation optics (22) and said measuring head (14) is decoupled with the laser (12) and/or with the spectrometer (26) via at least one optical waveguide (16, 18) arranged in said measuring head (14), said high-power laser comprising a frequency multiplying Nd:YAG type laser, and wherein a transmission switch (24) is provided between said spectrometer (26) and said radiation optics (22).

7. The device of claim 6 and wherein said transmission switch (24) comprises a Pockels cell.

8. A device for determining element compositions and concentrations of material samples and specifically for determining the concentration or the presence of precious metals in unsorted metal scrap, by means of laser-based plasma emission spectroscopy, said device comprising a high-power laser (12), a spectrometer (26), and at least one measuring head (14), said high-power laser (12) and said spectrometer (26) being geometrically and stereoscopically decoupled from said measuring head (14) wherein said measuring head (14) includes integrated radiation optics (22) and said measuring head (14) is decoupled with the laser (12) and/or with the spectrometer (26) via at least one optical waveguide (16, 18) arranged in said measuring head (14), said measuring head (14) including a casing and radiation optics provided in said casing wherein said casing (32) includes at least one movable spacer (34), said spacer (34)—in a first position thereof—partially projecting from the side of the casing (32) which faces the sample (20) to be measured, and—in a second position thereof—being completely inside the casing (32), said spacer (43)—in its second position—releasing a triggering means (38) for the laser (12).

9. The measuring head of claim 8 wherein the radiation optics (22) is mounted at a defined constant distance from an exit opening (36) of the casing (32) such that the focal point of the laser beam is in the plane of said exit opening (36).

10. The measuring head of claim 9 wherein the radiation optics (22) is mounted at a distance of 25 to 40 mm from the exit opening (36) of the casing (32).

* * * * *

UNITED STATES PATENT AND TRADEMARK OFFICE
CERTIFICATE OF CORRECTION

PATENT NO. : 5,798,832
DATED : August 25, 1998
INVENTOR(S) : Klaus D. Hnilica; Klaus Schneider It is certified that error appears in the above-identified patent and that said Letters Patent is hereby corrected as shown below:

On the title page; item [73]

Change Assignee: NIS Ingenieurgesselschaft MBH to
Assignee: NIS Ingenieurgesellschaft MBH Signed and Sealed this Twelfth Day of January, 1999

Attest:

*Attesting Officer*     *Acting Commissioner of Patents and Trademarks*